United States Patent [19]

Caullet et al.

[11] Patent Number: 5,215,736

[45] Date of Patent: Jun. 1, 1993

[54] MORDENITE TYPE ZEOLITE AND ITS PREPARATION PROCESS

[75] Inventors: Philippe Caullet, Illzach; Jean-Louis Guth, Brunstatt; Anne-Catherine Faust, Mulhouse; Jean-François Joly, Paris; Christine Travers, Rueil Malmaison; Francis Raatz, Acheres, all of France

[73] Assignee: Institut Francais du Petrole, France

[21] Appl. No.: 860,557

[22] Filed: Mar. 30, 1992

Related U.S. Application Data

[63] Continuation of Ser. No. 597,679, Oct. 10, 1990, abandoned.

[30] Foreign Application Priority Data

Oct. 10, 1989 [FR] France .............. 89 13317

[51] Int. Cl.$^5$ .............................. C01B 33/34
[52] U.S. Cl. .................... 423/700; 423/DIG. 25; 502/66; 208/135; 585/481
[58] Field of Search ........... 423/328, 329, 330, 700, 423/DIG. 25; 502/66; 208/135; 585/481

[56] References Cited

U.S. PATENT DOCUMENTS

| | | |
|---|---|---|
| 3,531,243 | 9/1970 | Aitken et al. .............. 423/329 |
| 3,597,155 | 8/1971 | Flanigen .................... 423/328 |
| 3,839,539 | 10/1974 | Elliott, Jr. ................. 423/329 |
| 3,849,340 | 11/1974 | Pollitzer .................... 423/328 |
| 4,073,865 | 2/1978 | Flanigen et al. ........... 423/329 |
| 4,444,738 | 4/1984 | Suzuki et al. .............. 423/329 |
| 4,501,656 | 2/1985 | Dufresne et al. ........... 208/111 |
| 4,525,466 | 6/1985 | Moretti et al. ............. 423/329 |
| 4,564,512 | 1/1986 | Baacke et al. ............. 423/328 |
| 4,687,654 | 8/1987 | Taramasso et al. ........ 423/328 |
| 4,789,655 | 12/1988 | Travers et al. ............. 502/66 |
| 4,853,203 | 8/1989 | Guth et al. ................. 423/328 |
| 4,902,847 | 2/1990 | Juguin et al. ............... 585/533 |
| 4,935,578 | 6/1990 | Dufresne et al. ........... 585/739 |
| 4,943,546 | 7/1990 | Travers et al. ............. 502/66 |
| 4,977,121 | 12/1990 | Dufresne et al. ........... 502/66 |
| 5,077,254 | 12/1991 | Travers et al. ............. 502/66 |

FOREIGN PATENT DOCUMENTS 0040104 11/1981 European Pat. Off. .

OTHER PUBLICATIONS

Kessler, Henri, "Studies in Surface Science and Catalysis", 52, *Recent Advances in Zeolite Science*, pp. 17–37.
Guth et al., "New Developments in Zeolite Science and Technology", New Route to *Pentasil-Type Zeolites . . . in the Presence of Fluoride Ions*, pp. 121–128.
Namba, "New Developments in Zeolite Science and Technology", *Shape, Selective Cracking . . . on HZSM-5*, pp. 661, 663.
Haag, "Proceedings of the Sixth International Zeolite Conference", Jul. 1983 *Acid Catalysis with Medium Pore Zeolites*, pp. 466 and 472.
Post et al., *An Infrared and Catalytic Study of Isomophous Substitution in Pentasil Zeolities*, pp. 368, 371.
Patent Abstracts of Japan, vol. 8, No. 134 (C-230) (1571), Jun. 21, 1984 (JP 59-46138).

*Primary Examiner*—R. Bruce Breneman
*Attorney, Agent, or Firm*—Millen, White, Zelano & Branigan

[57] ABSTRACT

The object of the invention is a synthetic crystalline zeolite of the mordenite type characterized by:
a) the following approximate general formula:

$$Na_2O, Al_2O_3, xSiO_2$$

where x is a number ranging from 9 to 30, and
b) an X-ray diffraction diagram represented in table I of the description,
c) a fluorine content ranging from about 0.005 to 2.0% by weight, and in that it has been synthetized in a fluoride medium.

The invention also relates to a process for preparing said zeolite.

This zeolite can notably be utilized in adsorption and in catalysis.

23 Claims, No Drawings

MORDENITE TYPE ZEOLITE AND ITS PREPARATION PROCESS

This application is a continuation of application Ser. No. 07/597,679, filed Oct. 10, 1990, now abandoned.

BACKGROUND OF THE INVENTION

The present invention relates to a new zeolite of the mordenite type and to a process for preparing this zeolite.

Because of their geometric selectivity and ion exchange properties, zeolites are utilized in industry on a large scale, in adsorption (for example gas drying, separation of linear and branched paraffins, separation of aromatic compounds, etc.) as well as in catalysis (for example catalytic cracking, hydrocracking, isomerization, oligomerization, etc.).

The chemical composition of the zeolites containing in their structure the elements Si and Al can be represented by the following approximate formula:

$$M_{2/n}O, Al_2O_3, xSiO_2$$

where M represents a cation of valence n, such as for example an alkaline, an alkaline-earth or an organic cation, x may range, according to the structures, between two and infinity, in which case the zeolite is a microporous silica.

Although numerous zeolites of the aluminosilicate type do exist in nature, the search for products with new properties has led to the synthesis of a large variety of these aluminosilicates of zeolitic structure including mordenites. Mordenite is a zeolite which crystallizes in the orthorhombic system with crystalline parameters a, b, c respectively close to 18 1, 20.5 and 7.5 Angströms (1 Angström=1 Å$10^{-10}$ meter) Its pore structure is monodimensional, the opening of the pores being delimited by cycles with 12 oxygens.

One of the first mordenite syntheses has been reported at the beginning of the sixties (A. KEOUGH and L. SAND, J. Am. Chem. Soc., Vol. 83, 1961, p. 3536): this synthesis is performed in an alkaline medium, the compensation cation being Na$^+$. The ratio Si/Al of this synthetic mordenite is close to the value known for natural mordenite, that is to say 5. Contrarily to the mordenites of natural origin, this synthetic variety belongs to the type with wide pores, that is to say that it has adsorption properties in accordance with its crystallographic structure. In an alkaline medium and in the absence of any organic structurers, the maximum ratios Si/Al are close to 10 (O. WHITTEMORE, Am. Mineralogist, Vol. 57, 1972, p. 1146 P. BODART, J. B. NAGY, E. DEROUANE, Z. GABELICA, Stud. Surf. Sci. Catal., Vol. 18, 1984, p. 125). The use of cations or of organic molecules in the alkaline reaction mixture has allowed to synthetize mordenites with a ratio Si/Al higher than 10. It should be noted that, in these syntheses in the presence of organic agents, the sodium cation is always associated with the synthesis medium. Among these syntheses in the presence of organic compounds, the following patents can for example be cited : JP58 88,118, US-A 4,052,472, EP-A 80,615, US-A 4,525,466.

All the mordenite type zeolites which have been prepared until presently have been synthetized in a conventional medium, that is to say in an alkaline medium with a pH value generally higher than 9, a medium in which the mobilizing agent of the silica is the OH$^-$ anion. Another synthesis medium of the zeolites has been discovered recently : it is the fluoride medium, in which the mobilizing agent of silica is the F$^-$ anion; in this medium, the pH value is generally lower than 10 (see for example J. L. GUTH, H. KESSLER and R. WEY, Proc. 7th Int. Zeolite Conf., Tokyo, August 17-22 1986, p. 121). The synthesis of a limited number of zeolitic structures has already been successful in this new medium, as for example MFI (French Patent Application 88/09,631) and ferrierite (French Patent Application 86/16,362).

In relation to the alkaline synthesis medium (OH$^-$), the fluoride medium shows a certain number of very appreciable advantages. In fact, in an alkaline medium, most synthetized zeolites are metastable : more stable solid phases are therefore likely to appear during the synthesis and unwanted phases may be precipitated. This difficulty increases when the amounts to be prepared are higher, that is to say by passing from the laboratory stage to the industrial stage. Besides, these metastable zeolites in the basic reaction medium are obtained only through a strong supersaturation of active species in the medium. This causes a rapid nucleation and consequently leads to crystals with small sizes, the average dimensions of these crystals ranging around one micrometer. Developing crystals with a larger size is therefore difficult in a basic medium. But, in certain applications, it may be interesting to have crystals with a larger size in order to preserve for example the thermal stability of the solid.

Besides, the chemistry of the aluminosilicate species in a fluoride medium is totally different from that which is known in the conventional alkaline medium. Syntheses in a fluoride medium may thus lead to solids the local Si-Al distribution of which in the structure is different from that which is known for zeolites synthetized in a conventional medium. This point is of particular importance in the case of mordenite. As a matter of fact, the aluminum is preferably located, for mordenites known in prior art, in the 4 membered rings of the structure (V. GRAMLICH, Ph.D, Dissertation ETH n° 4633, Zurich, 1971; G. DEBRAS, J. B. NAGY, Z. GABELICA, P. BODART, P. A. JACOBS, Chem. Lett, 1983, p. 199); pairing 2 atoms of aluminum in each cycle is thermodynamically favored (E. G. DEROUANE, J. G. FRIPIAT, Proc. 6th Int. Zeolite Conf., Reno, USA, 1984, p. 717). This situation has two drawbacks : on one hand, the proximity of the atoms of aluminum tends to limit the force of the acid sites of the H forms and, on the other hand, the presence of such Al—Al pairs, even in the dealuminized H forms, is translated into poor selectivities in certain reactions for which the bi-site reactions should be banished (example of the isomerization of the aromatic C8). Preparing mordenites with a lower content of Al—Al pairs thus appears as a particularly interesting way of improvement.

OBJECT OF THE INVENTION

The object of the invention is thus a new synthetic crystalline zeolite of the mordenite type, a process for the synthesis of said zeolite in which the disadvantages cited above are avoided and which also gives the zeolites according to the invention improved properties, particularly acid properties. The new type of zeolite according to the invention can be notably used in adsorption and in catalysis, especially in the isomerization of xylenes.

DETAILED DESCRIPTION OF THE INVENTION

The mordenite type zeolite according to the invention has (after synthesis) the following approximate general formula:

$$Na_2O, Al_2O_3, xSiO_2.$$

The zeolite according to the invention is notably characterized by:
a) a number x ranging from 9 to 30, preferably from 9 to 20, in a more preferred manner from 9 to 15 (x being the molar ratio $SiO_2/Al_2O_3$),
b) an X-ray diffraction diagram represented in table I of the description,
c) a fluorine content ranging from about 0.005 to 2.0 % by weight, preferably from about 0.01 to 1.5 % by weight, in a more preferred manner from about 0.10 to 1.5 % by weight.

It is also characterized in that it has been synthetized in a fluoride medium.

This new mordenite type zeolite according to the invention generally shows at least a crystal size ranging from 0.10 to 5 $\mu m$ and preferably from 1 to 2 $\mu m$ (1 $\mu m = 10^{-6}$ meter).

The invention also relates to a process for preparing said zeolite of the mordenite type, which involves in:
a) forming a dissolved reaction mixture with a pH value lower than about 10 and comprising water, at least one silica source, at least one aluminum source, at least one source of a mobilizing agent containing fluoride ions ($F^{-1}$), one source of sodium cations ($Na^+$), said reaction mixture having a composition, expressed in molar ratio, ranging between the following values:
Si/Al:5–50, preferably 5–25,
$F^-$/Si:0.1–10, preferably 0.25–8,
$Na^+$/Si:0.1–10, preferably 0.25–8,
$H_2O$/Si:5–25,
b) maintaining said reaction mixture at a heating temperature ranging from about 90° to about 250° C., preferably from about 130° to about 220° C., until a crystalline compound is obtained.

The reaction mixture can be advantageously heated in an autoclave fitted with a polytetrafluoroethylene (PTFE) inner lining between about 90° and about 250° C. an preferably between about 130° and about 220° C., for a duration which may range from several hours to several days (usually 8 to 1,200 hours) according to the chosen reaction temperature, until a crystallized solid is obtained, which is generally separated from the mother liquors by filtering and which is then washed for example with distilled water.

Said reaction mixture can be advantageously prepared at a pH value ranging from about 4 to about 10 and, preferably, from about 6 to about 10.

According to a preferred preparation embodiment of the mordenite zeolites according to the invention, the molar ratios of the reaction mixture constituents range between the following values:
Si/Al:6.5–15
$F^-$/Si:0.4–5
$Na^+$/Si:0.4–5
$H_2O$/Si:8–22.

It is possible to add to said reaction mixture at least one additional salt in a molar ratio additional salt to $SiO_2$ generally ranging from 0.1 to 4 and preferably from 0.2 to 0.5 and/or at least one nucleus of the zeolite formed according to the invention in a proportion by weight of zeolite crystal to $SiO_2$ generally ranging from 0.01 to 0.1 and preferably from 0.02 to 0.03, so that the morphology, the crystal size and the kinetics of the crystallization reaction can be advantageously controlled.

It can be advantageously operated in a stirred medium, which may allow to considerably decrease the reaction time.

The pH of the reaction medium, lower than about 10, can be obtained either directly from one or several ones of the utilized reagents, or by adding an acid, a base, an acid salt, a basic salt or an additional buffer mixture.

Numerous silica sources can be used. The following can be notably cited: silicas in the form of hydrogels, of aerogels, of pseudosolutions, as well as the silicas resulting from the precipitation of soluble silicate solutions or from the hydrolysis of silicic esters such as orthosilicic acid tetraethylic ester $Si(OC_2H_5)_4$ or of complexes such as sodium fluorosilicate $Na_2SiF_6$ or ammonium fluorosilicate $(NH_4)_2SiF_6$.

Among the aluminum sources that are utilized, hydrated aluminum chloride ($AlCl_3$, $6H_2O$), nonahydrated aluminum nitrate ($Al(NO_3)_3$, $9H_2O$), aluminum sulfate with 16 molecules of water or trihydrated aluminum fluoride ($AlF_3$, $3H_2O$ will be preferably selected Pseudoboehmite can also be cited.

Instead of starting from separate sources of silica and aluminum, it is also possible to use sources where both elements are combined, such as, for example, a freshly precipitated aluminosilicate gel.

The fluoride anions $F^-$ can be introduced in the form of salts of sodium or of ammonium or of alkaline metals such as, for example, $NaF$, $NH_4F$, $NH_4HF_2$ or in the form of an HF acid or in the form of hydrolysable compounds that can release fluoride anions in water such as silicon fluoride $SiF_4$ or ammonium fluorosilicate $(NH_4)_2SiF_6$ or sodium fluorosilicate $Na_2SiF_6$.

The acids or acid salts, the bases or basic salts that are possibly added as a complement in order to bring the pH of the reaction medium to the wanted value can be selected among the usual acids such as, for example, HF, HCl, $HNO_3$, $H_2SO_4$, $CH_3COOH$ or the acid salts such as, for example, $NH_4HF_2$, $KHF_2$, $NaHSO_4$, the usual bases such as, for example, $NaHCO_3$, $CH_3COONa$, $Na_2S$, $NaHS$ or the buffer mixtures such as, for example, ($CH_3COOH$, $CH_3COONa$) or ($NH_4OH$, $NH_4Cl$).

It is possible to introduce into the zeolite of the mordenite structure according to the invention, through ion exchange techniques well-known in prior art, at least one element of the periodic table the cations of which can be prepared in an aqueous medium and selected for example from the family consisting of groups IIA, IIIA, IB, IIB, IIIB, IVB and VIIIA of the periodic table of elements. Examples such as the alkaline and alkaline-earth cations, the rare-earth cations, $Fe^{II}$, $Fe^{III}$, $Co^{II}$, $Co^{III}$, $Ni^{II}$, $Cu^{II}$, $Zn^{II}$, $Ag^{I}$, $Pt^{II}$ can be cited.

Identifying zeolites of the mordenite type according to the invention can be easily done from their X-ray diffraction diagram. This diffraction diagram can be obtained by means of a diffractometer by using the conventional powder method with the K $\alpha$ radiation of copper. An inner standard allows to precisely determine the values of the angles 2 $\sigma$ associated with the diffraction peaks. The different interreticular distances $d_{hkl}$, characteristic of the sample, are calculated from Bragg's relationship. The measuring error estimation Δ(d_{hkl}) to d_{hkl} is calculated according to the absolute error Δ (2 σ) assigned to the measuring of 2 σ by Bragg's relationship. In the presence of an inner standard, this error is minimized and considered usually equal to ±0.05°. The relative intensity I/Io assigned to each value of d_{hkl} is estimated from the height of the corresponding diffraction peak. The latter one can also be determined from a picture obtained with a Debye-Scherrer chamber. A scale of symbols is often used to characterize this intensity: FF=very strong, F=strong, mF=average to strong, m=average, mf =average to weak, f=weak, ff=very weak.

Table I represents the X-ray diffraction diagram characteristic of the zeolites of the mordenite type according to the invention. In the d_{hkl} column, the extreme values which can be taken by the different interreticular distances d_{hkl} are represented. Each one of these values must be assigned the measuring error Δ (d_{hkl}) which usually ranges from ±0.07 to ±0.002 according to the value of 2 σ (d_{hkl} is expressed in Angströms, 1 Å=10^{-10} m).

The zeolite of mordenite structure according to the invention can be utilized alone or mixed with a matrix within a catalyst.

Said zeolite can for example, after synthesis, be shaped by using a matrix which may be inert or active for the reaction to be promoted. The matrixes that are used are generally selected from the group consisting of clays, aluminas, silica, magnesia, zircon, titanium oxide, boron oxide and any combination of at least two of the compounds cited above, such as silica-alumina, silica-magnesia, etc. All the well-known tableting and shaping methods are applicable, such as for example extrusion, pelleting, oil drop, etc.

The catalyst then shows a proportion by weight of zeolite of the mordenite type according to the invention generally ranging from 20 to 99.5%, preferably from 40 to 95%, and a proportion by weight of matrix generally ranging from 0.5 to 80%, preferably from 5 to 60%.

The catalyst containing the zeolite of the mordenite structure according to the invention may also comprise a hydrogenizing or a dehydrogenizing function, generally consisting of at least one metal or/and compound of metal selected from groups IA, VIB (Cr, Mo, W) and VIII from the periodic table of elements, for example platinum, palladium or/and nickel.

The zeolite of the mordenite structure according to the invention can be utilized, alone or mixed with a matrix (and generally a hydrogenizing or dehydrogenizing function within a catalyst , in a process for isomerizing xylenes. The operating conditions of said process are usually the following:
- temperature ranging from 240° to 600° C., preferably from 350° to 510° C.,
- pressure ranging from 0.5 to 100 bars, preferably from 2 to 30 bars,
- space velocity (WHSV), in mass of feedstock per unit of catalyst feedstock and per hour, ranging from 0.5 to 200 (hour)^{-1}, preferably from 2 to 100 (hour)^{-1},
- molar ratio hydrogen to hydrocarbons (H_2/HC) of the feedstock ranging from 0.5 to 12, preferably from 2 to 6.

TABLE I

| 2 θ (°) | d_{hkl} (Å) | I/Io |
| --- | --- | --- |
| 6.38 | 13.84 | mF |
| 8.50 | 10.39 | mf |
| 9.60 | 9.21 | F |
| 13.38 | 6.61 | mF |
| 13.70 | 6.46 | m |
| 14.35 | 6.17 | ff |
| 15.10 | 5.86 | f |
| 19.48 | 4.55 | mF |
| 20.72 | 4.28 | ff |
| 22.15 | 4.01 | F |
| 23.00 | 3.86 | ff |
| 23.50 | 3.78 | f |
| 24.30 | 3.66 | ff |
| 25.55 | 3.48 | FF |
| 26.20 | 3.398 | F |
| 27.65 | 3.223 | mF |
| 30.75 | 2.905 | m |
| 32.6 | 2.744 | ff |
| 33.08 | 2.706 | ff |
| 34.93 | 2.566 | ff |
| 35.55 | 2.523 | f |
| 40.39 | 2.231 | ff |
| 44.3 | 2.088 | f |

The following examples illustrate the invention without limiting the scope thereof.

EXAMPLE 1

0.93 g of NaF (0.0224 mole) are dissolved at room temperature in 9.36 g of water (0.52 mole);

3.73 g of "Na+ tixolex 28" (ratio Si/Al=7)

(0.052 mole $SiO_2$ and $7.43 \cdot 10^{-3}$ mole Al) and about 60 mg of crushed Na+-mordenite (about 2% by weight of the utilized silica) are then successively added, under stirring, to this solution.

After about ten minutes of stirring, the mixture is transferred into a 75-ml autoclave fitted with a Teflon inner lining. The autoclave is then directly placed into an oven for 7 days at 200° C.

The molar ratios of the reaction mixture are the following:

Si/Al=7; F−/Si=0.43; Na+/Si=0.57;
H_2O/Si=10.

The pH value of the reaction mixture is 9.5.

After the synthesis, the solid is recovered by filtration, washed with distilled water, dried in an oven at 80° C. for 24 hours and then subjected to an X-ray diffraction analysis.

The product is totally crystallized in the form of a mordenite, no impurity being detected on the diffractogram. The crystals show in the form of small "sticks" of 1 to 2 μm by some tenths of micron wide.

The fluorine content of the product is 0.16% by weight.

The molar ratio $SiO_2/Al_2O_3$ of the product, chemically determined, is 13.6. Considering the weight of the obtained mordenite, that is about 3 g, the reaction yield is high and close to 80% in relation to the weight of silica used.

EXAMPLE 2

Identical to example 1, but with 1.75 g NaF utilized (0.0416 mole) (molar ratio F−/Si=0.8); the fluorine content of the obtained product is 0.20% by weight.

EXAMPLE 3

Identical to example 1, but with 5.24 g NaF utilized (0.125 mole) (molar ratio F⁻/Si=2.4); the fluorine content of the obtained product is 0.25% by weight.

EXAMPLE 4

Identical to example 1, but with 10.5 g NaF utilized (0.250 mole) (molar ratio F⁻/Si=4.8).

EXAMPLE 5

Identical to example 1, but in the absence of NaF (molar ratio F⁻/Si=0).

Summary table of examples 1 to 5

| Example | Molar ratio F⁻/Si in the reaction mixture | Obtained product | | | |
|---|---|---|---|---|---|
| | | Nature | Molar ratio $SiO_2/Al_2O_3$ | Wt. (g) | Crystal size (μm) |
| 1 | 0.43 | 100% crystallized mordenite | 13.6 | 3 | 1–2 |
| 2 | 0.80 | 100% crystallized mordenite | 13.6 | 2.8 | 2 |
| 3 | 2.40 | 100% crystallized mordenite | 13.2 | 3.1 | 1 |
| 4 | 4.80 | 100% crystallized mordenite | 13.4 | 3.2 | 1–2 |
| 5 | 0 | gel | — | — | — |

EXAMPLE 6

The synthesis conditions are identical to those in example 1, except that 2.62 g of NaF (0.0624 mole) are utilized (molar ratio F⁻/Si=1.2) and that the reaction mixture is brought to 170° C. for 14 days. The pH value of the reaction mixture is about 9.5.

About 3.1 g of a well-crystallized mordenite in the form of crystals with a size ranging between about 1 to 2 μm are obtained.

EXAMPLE 7

The synthesis conditions are identical to those in example 1, except that 2.62 g of NaF (0.0624 mole) are utilized (molar ratio F⁻/Si=1.2) and that the synthesis temperature is 135° C. and the duration 21 days. The pH value of the reaction mixture is about 9.5. The obtained product is totally crystallized in the form of a mordenite, the crystal size ranging between 1 and 2 μm.

EXAMPLE 8

The synthesis conditions are identical to those in example 1, except that 2.62 g of NaF (0.0624 mole) are utilized (molar ratio F⁻/Si=1.2) and that the silicon source is of the aerosil type (Degussa). 3.12 g of aerosil are used, that is to say 0.052 mole of silicon. The alumina source is of the pseudoboehmite type. 0.60 g of pseudoboehmite are used, that is to say 7.5.10⁻³ mole of aluminum. The molar ratio H₂O/Si=20. The pH value of the reaction mixture is about 7. After the reaction, the pH value is about 9.5. The obtained product is totally crystallized in the form of a mordenite; the length of the crystals is about 2 μm.

EXAMPLE 9

The synthesis conditions are identical to those in example 1, except that the synthesis duration is 4 days at a temperature of 200° C. The pH value of the reaction mixture is about 9.5. After the synthesis, the pH value is also 9.5.

The mass of recovered product is about 3 g; the gel is totally converted into mordenite (obtained mass: 3 g; crystal size: 1–2μm).

EXAMPLE 10

63 g of NaF, that is to say 1.5 mole of NaF, are dissolved at room temperature; 134.19 g of Tixolex 28 (ratio Si/Al=7), that is to say 1.87 mole of $SiO_2$ and 0.267 mole of aluminum and about 2.23 g of crushed Na⁺-mordenite (that is to say about 2% by weight of the silica used), are added to this solution under stirring.

After 30 minutes of stirring, the reaction mixture, with a pH value of 9.7, is transferred into 75 ml autoclaves fitted with Teflon inner linings.

The reaction mixture shows the following molar composition:

$$Si/Al=7; \ F^-/Si=0.8; \ H_2O/Si=10.$$

The reaction mixture is brought to 200° C. for 5 days. After the reaction, the pH value is 10. After filtering and washing with distilled water, the solid is dried in an oven at 80° C. for 24 hours and then subjected to an X-ray diffraction analysis.

The product is crystallized in the form of a mordenite. Its molar ratio $SiO_2/Al_2O_3$, chemically determined, is 14.5.

EXAMPLE 11

Preparation of a catalyst

The mordenite obtained in example 10 is then intimately mixed with alumina on which 0.45% by weight of platinum has been dispersed. The support consists of the mixture mordenite-alumina containing 40% by weight of alumina. The content by weight of platinum in the final catalyst is 0.18%.

The catalyst manufactured thereby is then shaped by pelletizing, calcined under air up to 550° C. for 2 hours and reduced under hydrogen at 450° C. for 3 hours.

EXAMPLE 12

The catalyst described in example 11 is implemented in the isomerization reaction of orthoxylene, at a temperature of 410° C., under a pressure of 12 bars, with a space velocity (WHSV) of 35 (hour)⁻¹ and a ratio H₂/HC of about 4. The performance of this catalyst, and of that which will be described in the following example, presented in table II, are defined by:

Approach to equilibrium of o.x
(calculated from the mixture of the 3 xylenes) =

$$\frac{\text{Mass of o.x in the feedstock} - \text{Mass of o.x in the end product}}{\text{Mass of o.x in the feedstock} - \text{Mass of o.x at equilibrium}} \times 100$$

Approach to equilibrium of p.x
(calculated from the mixture of the 3 xylenes) =

-continued $$\text{Aromatic } C_8 \text{ and naphthenic } C_8 \text{ yield} = \frac{\frac{\text{Mass of p.x in the end product}}{\text{Mass of p.x at equilibrium}} \times 100}{}$$

$$\text{Aromatic } C_8 \text{ and naphthenic } C_8 \text{ yield} = \frac{\text{Mass of arom. } C_8 \text{ in end pro.} + \text{Mass of napth. } C_8 \text{ in end pro.}}{\text{Total end product mass}} \times 100$$

Dismutation % =

$$(\% \text{ by wt of } C_9 \text{ in the end product}) \left( 1 + \frac{C_7 \text{ molar weight}}{C_9 \text{ molar weight}} \right) +$$

$$(\% \text{ by wt of } C_{10} \text{ in the end product}) \left( 1 + \frac{C_6 \text{ molar weight}}{C_{10} \text{ molar weight}} \right)$$

Dealkylation % = (% by wt of $C_6$ in the end product) −

$$(\% \text{ by wt of } C_{10} \text{ in the end product}) \left( \frac{C_6 \text{ molar weight}}{C_{10} \text{ molar weight}} \right) +$$

(% by wt of $C_7$ in the end product) −

$$(\% \text{ by wt of } C_9 \text{ in the end product}) \left( \frac{C_7 \text{ molar weight}}{C_9 \text{ molar weight}} \right)$$

Cracking % = % by wt of $(C_3 + C_4 + C_5)$ in the end product (with o.x = o-xylene and p.x = p-xylene).

EXAMPLE 13
Comparison

A catalyst is prepared with a wide-pore mordenite in the form of a powder referenced Zeolon 100 Na manufactured by the Norton company. The powder is subjected to 3 exchanges with a 4M ammonium nitrate solution. Each exchange is performed for ½ hour at the reflux temperature.

After the last exchange, the product is washed with water for 20 mn, filtered and dried in an oven at 120° C.. Its molar ratio $SiO_2/Al_2O_3$ is 13 and its sodium content is 75 ppm.

The preparation of the catalyst and the catalytic test are achieved under the conditions described in examples 11 and 12.

The catalytic results appear in table II.

The mordenite synthetized in a fluoride medium according to the invention leads to a more selective catalyst, the side reactions and particularly the dismutation and cracking reactions are considerably inhibited. This result might be explained by a distribution of the atoms of aluminum that is different in the two solids.

TABLE II

| Catalyst | A | B |
|---|---|---|
| A.E. o.x (*) | 65.2 | 66.0 |
| aro + naphth $C_8$ yield | 94.1 | 94.5 |
| A.E. p.x (**) | 44.6 | 50 |
| Dismutation % | 1.25 | 4.4 |
| Dealkylation % | 0.06 | 0.15 |
| Cracking % | 0.2 | 0.5 |

(*) approach to equilibrium of orthoxylene
(**) approach to equilibrium of paraxylene.

We claim:

1. A process for making a synthetic crystalline mordenite zeolite having:
   a) the following approximate general formula:

$Na_2O: Al_2O_3: xSiO_2$ where x is a number ranging from 9 to 30, an X-ray diffraction pattern as follows

| $2\theta$ (°) | $d_{hkl}$ (Å) | $I/I_o$ |
|---|---|---|
| 6.38 | 13.84 | mF |
| 8.50 | 10.39 | mf |
| 9.60 | 9.21 | F |
| 13.38 | 6.61 | mF |
| 13.70 | 6.46 | m |
| 14.35 | 6.17 | ff |
| 15.10 | 5.86 | f |
| 19.48 | 4.55 | mF |
| 20.72 | 4.28 | ff |
| 22.15 | 4.01 | F |
| 23.00 | 3.86 | ff |
| 23.50 | 3.78 | f |
| 24.30 | 3.66 | ff |
| 25.55 | 3.48 | FF |
| 26.20 | 3.398 | F |
| 27.65 | 3.223 | mF |
| 30.75 | 2.905 | m |
| 32.6 | 2.744 | ff |
| 33.08 | 2.706 | ff |
| 34.93 | 2.566 | ff |
| 35.55 | 2.523 | f |
| 40.39 | 2.231 | ff |
| 44.3 | 2.088 | f | and
   c) a fluorine content ranging from about 0.005% to 20%,
said process comprising reacting in a dissolved reaction mixture at least one source of sodium cations, at least one source of aluminum, at least one source of silica, and at least one source of a silica mobilizing agent containing fluoride ions at a pH lower than about 9 to obtain said crystalline mordenite zeolite.

2. The process according to claim 1 wherein said pH ranges from about 6 to about 9.

3. The process according to claim 1 wherein said pH is lower than 7.

4. The zeolite produced by the process of claim 1.

5. The zeolite produced by the process of claim 2.

6. The zeolite produced by the process of claim 3.

7. The zeolite produced by the process of claims 1, 2, or 3 wherein x is a number ranging from 9 to 20.

8. The zeolite according claim 7 wherein x is a number ranging from 9 to 15.

9. The zeolite according to any one of the claims 1, 2, or 3 having a fluorine content ranging from about 0.01% to 1.5% by weight.

10. A catalyst composition comprising a zeolite according to any one of claims 1, 2, or 3 and a matrix.

11. A catalyst composition comprising a zeolite according to any one of claims 1, 2, or 3, a matrix and at least one metal or/and compound of metal selected from the groups consisting of IA, VIB and VIII of the periodic table of elements.

12. The process according to claim 1 wherein the reaction mixture used to form said zeolite has a composition, expressed in molar ratios, ranging between the following values:
Si/Al:5–50
$F^-/Si$:0.1–10
$Na^+/Si$:0.1–10

H₂O/Si:5-25, and wherein said reaction mixture is heated to a temperature ranging from about 90° C. to about 250° C. and maintained until said zeolite is obtained.

13. The process according to claim 12 wherein the pH of the reaction mixture ranges from about 6 to about 9.

14. The process according to claim 12 wherein the pH of the reaction mixture is less than 7.

15. The process according to claim 12 wherein said reaction mixture has a composition, expressed in molar ratios, ranging between the following values:

Si/Al:5-25
F⁻/Si:0.25-8
Na⁺/Si:0.25-8
H₂O/Si:8-25.

16. The process according to claim 15 wherein said reaction mixture has a composition, expressed in molar ratios, ranging between the following values:

Si/Al:6.5-15
F⁻/Si:0.4-5
Na⁺/Si:0.4-5
H₂O/Si:8-22.

17. The process according to claim 12 wherein said reaction mixture is heated to a temperature ranging from about 130° to 220° C. and maintained until; said zeolite is obtained.

18. The zeolite produced by the process of claim 13.

19. The zeolite produced by the process of claim 14.

20. A process for the catalytic isomerization of xylenes comprising contacting a feed mixture containing xylenes under xylene isomerization conditions with a catalyst composition comprising the zeolite of claim 4.

21. The process according to claim 20 wherein said catalyst consists essentially of said zeolite and a matrix.

22. A process for the catalytic isomerization of xylenes of xylenes comprising contacting a feed mixture containing xylenes under xylene isomerization conditions with a catalyst composition comprising the zeolite of claim 18.

23. The process according to claim 22 wherein said catalyst consists essentially of said zeolite and a matrix.

* * * * *